US009597301B2

(12) United States Patent
Wen et al.

(10) Patent No.: US 9,597,301 B2
(45) Date of Patent: *Mar. 21, 2017

(54) PROPYNYLAMINOINDAN TRANSDERMAL COMPOSITIONS

(71) Applicant: Teikoku Pharma USA, Inc., San Jose, CA (US)

(72) Inventors: Jianye Wen, Palo Alto, CA (US); Richard D. Hamlin, Newark, CA (US)

(73) Assignee: Teikoku Pharma USA, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/659,130

(22) Filed: Mar. 16, 2015

(65) Prior Publication Data

US 2015/0182476 A1 Jul. 2, 2015

Related U.S. Application Data

(63) Continuation of application No. 13/052,955, filed on Mar. 21, 2011, now Pat. No. 9,017,723.

(60) Provisional application No. 61/330,018, filed on Apr. 30, 2010.

(51) Int. Cl.
| | |
|---|---|
| A61K 9/70 | (2006.01) |
| A61K 31/165 | (2006.01) |
| A61K 31/135 | (2006.01) |
| A61K 31/137 | (2006.01) |
| A61K 9/00 | (2006.01) |

(52) U.S. Cl.
CPC .......... *A61K 31/135* (2013.01); *A61K 9/0014* (2013.01); *A61K 9/7053* (2013.01); *A61K 9/7061* (2013.01); *A61K 9/7069* (2013.01); *A61K 31/137* (2013.01)

(58) Field of Classification Search
None
See application file for complete search history.

(56) References Cited

U.S. PATENT DOCUMENTS

| | | | |
|---|---|---|---|
| 4,452,808 A | 6/1984 | Gallagher | |
| 4,588,740 A | 5/1986 | Gallagher | |
| 4,824,860 A | 4/1989 | Owen | |
| 4,912,126 A | 3/1990 | Owen | |
| 5,176,916 A | 1/1993 | Yamanaka et al. | |
| 5,387,612 A | 2/1995 | Youdim et al. | |
| 5,391,406 A | 2/1995 | Ramharack et al. | |
| 5,422,123 A | 6/1995 | Conte et al. | |
| 5,453,446 A | 9/1995 | Youdim et al. | |
| 5,457,133 A | 10/1995 | Youdim et al. | |
| 5,462,746 A | 10/1995 | Wolter et al. | |
| 5,519,061 A | 5/1996 | Youdim et al. | |
| 5,532,415 A | 7/1996 | Youdim et al. | |
| 5,543,151 A | 8/1996 | Shirai et al. | |
| 5,576,353 A | 11/1996 | Youdim et al. | |
| 5,599,991 A | 2/1997 | Youdim et al. | |
| 5,650,165 A | 7/1997 | Akemi et al. | |
| 5,668,181 A | 9/1997 | Youdim et al. | |
| 5,683,710 A | 11/1997 | Akemi et al. | |
| 5,744,500 A | 4/1998 | Youdim et al. | |
| 5,786,390 A | 7/1998 | Youdim et al. | |
| 5,807,570 A | 9/1998 | Chen et al. | |
| 5,830,497 A | 11/1998 | Yamanaka et al. | |
| 5,891,923 A | 4/1999 | Youdim et al. | |
| 6,126,968 A | 10/2000 | Peskin et al. | |
| 6,132,761 A | 10/2000 | Muraoka et al. | |
| 6,146,656 A | 11/2000 | Hori et al. | |
| 6,198,017 B1 | 3/2001 | Basedow et al. | |
| 6,218,421 B1 | 4/2001 | King | |
| 6,231,885 B1 | 5/2001 | Carrara | |
| 6,262,330 B1 | 7/2001 | Fujisawa et al. | |
| 6,300,365 B1 | 10/2001 | Holman | |
| 6,316,504 B1 | 11/2001 | Youdim et al. | |
| 6,528,685 B2 | 3/2003 | Cohen et al. | |
| 6,562,363 B1 | 5/2003 | Mantelle et al. | |
| 6,630,514 B2 | 10/2003 | Youdim et al. | |
| 6,638,528 B1 | 10/2003 | Kanios | |
| 6,689,379 B1 | 2/2004 | Bracht | |
| 6,809,120 B1 | 10/2004 | Warrington et al. | |
| 6,929,801 B2 | 8/2005 | Klose et al. | |
| 6,936,661 B2 | 8/2005 | Koch et al. | |

(Continued)

FOREIGN PATENT DOCUMENTS

| | | |
|---|---|---|
| CN | 101001616 A | 7/2007 |
| CN | 101032474 A | 9/2007 |

(Continued)

OTHER PUBLICATIONS

Schurad et al., Evaluation of the transdermal permeation behavior of Proterguride from drug in adhesive matrix patches through hairless mouse skin, Drug Dev Ind Pharm (2005), 31(6):505-13.
Furuishi et al, "Formulation and in Vitro Evaluation of Pentazocine Transdermal Delivery System", Biol. Pharm. Bull., 2008, 31(7):1439-1443.
Am et al., Contrasting neuroprotective and neurotoxic actions of respective metabolites of anti-Parkinson drugs rasagiline and selegiline, Neurosci Lett. Jan. 30, 2004;355(3):169-72.
DURO-TAK and GELVA Transdermal Pressure Sensitive Adhesives, Product Selection Guide, Henkel, obtained online at: http://www.henkelna.com/us/content_data/330922_11061_LT5343_Product_selector2_Web863600.pdf, downloaded on Dec. 27, 2014.

*Primary Examiner* — H. Sarah Park
(74) *Attorney, Agent, or Firm* — Khin K. Chin; Bret E. Field; Bozicevic, Field & Francis LLP

(57) ABSTRACT

Propynylaminoindan (e.g., Rasagiline) transdermal compositions are provided. Aspects of the transdermal compositions include a matrix of the propynylaminoindan in a pressure sensitive adhesive comprising a carboxylated polymer. In some instances, the matrix further includes a cationic acrylic copolymer. Also provided are methods of using the transdermal compositions and kits containing the transdermal compositions.

7 Claims, 8 Drawing Sheets

(56) References Cited

U.S. PATENT DOCUMENTS

| | | |
|---|---|---|
| 6,956,060 B2 | 10/2005 | Youdim et al. |
| 6,972,376 B2 | 12/2005 | Hughey et al. |
| 7,070,808 B2 | 7/2006 | Govil et al. |
| 7,150,881 B2 | 12/2006 | Govil et al. |
| 7,175,853 B1 | 2/2007 | Bracht |
| 7,220,473 B2 | 5/2007 | Beier et al. |
| 7,335,379 B2 | 2/2008 | Carrara et al. |
| 7,375,249 B2 | 5/2008 | Boulton et al. |
| 7,378,439 B2 | 5/2008 | Tarur et al. |
| 7,396,860 B2 | 7/2008 | Blaugrund et al. |
| 7,491,847 B2 | 2/2009 | Frenkel et al. |
| 7,572,834 B1 | 8/2009 | Sterling et al. |
| 7,598,420 B1 | 10/2009 | Sterling et al. |
| 7,638,140 B2 | 12/2009 | Govil et al. |
| 7,989,496 B2 | 8/2011 | Hartwig et al. |
| 2003/0212085 A1 | 11/2003 | McCall et al. |
| 2004/0013620 A1 | 1/2004 | Klose et al. |
| 2004/0253299 A1 | 12/2004 | Beier et al. |
| 2005/0142175 A1 | 6/2005 | Langguth et al. |
| 2005/0175680 A1 | 8/2005 | Morgan et al. |
| 2005/0186141 A1 | 8/2005 | Gonda et al. |
| 2005/0187283 A1 | 8/2005 | Drago |
| 2005/0191348 A1 | 9/2005 | Youdim et al. |
| 2005/0245617 A1 | 11/2005 | Meyerson et al. |
| 2005/0267176 A1 | 12/2005 | Barberich |
| 2006/0078604 A1 | 4/2006 | Kanios et al. |
| 2006/0188581 A1 | 8/2006 | Peskin |
| 2007/0026054 A1 | 2/2007 | Theobald et al. |
| 2007/0078172 A1 | 4/2007 | McElroy et al. |
| 2007/0093495 A1 | 4/2007 | Ruggero et al. |
| 2007/0225379 A1 | 9/2007 | Carrara et al. |
| 2007/0254941 A1 | 11/2007 | Kumar et al. |
| 2007/0264319 A1 | 11/2007 | Lebo et al. |
| 2008/0004329 A1 | 1/2008 | Jamieson et al. |
| 2008/0089859 A1 | 4/2008 | Holman |
| 2008/0161408 A1 | 7/2008 | Frenkel et al. |
| 2008/0220092 A1 | 9/2008 | DiPierro et al. |
| 2008/0292708 A1 | 11/2008 | Stefanelli et al. |
| 2009/0035377 A1 | 2/2009 | Houze |
| 2009/0043111 A1 | 2/2009 | Liu |
| 2009/0062400 A1 | 3/2009 | Oron et al. |
| 2009/0076160 A1 | 3/2009 | Lendvai et al. |
| 2009/0136549 A1 * | 5/2009 | Lin ................. A61K 9/7053 424/400 |
| 2009/0136555 A1 | 5/2009 | Crowley et al. |
| 2009/0155343 A1 | 6/2009 | Kawahara et al. |
| 2009/0291127 A1 | 11/2009 | Wen et al. |
| 2009/0318564 A1 * | 12/2009 | Frenkel ............. A61K 31/136 514/657 |
| 2010/0010095 A1 | 1/2010 | Frenkel |
| 2010/0016442 A1 | 1/2010 | Cohen et al. |
| 2010/0029987 A1 | 2/2010 | Allegrini et al. |
| 2010/0040690 A1 | 2/2010 | Govil et al. |
| 2010/0087768 A1 | 4/2010 | Forlano et al. |
| 2010/0285133 A1 | 11/2010 | Choi |
| 2011/0002976 A1 | 1/2011 | Yamamoto et al. |
| 2011/0268785 A1 | 11/2011 | Wen et al. |
| 2012/0265158 A1 | 10/2012 | Braun et al. |
| 2013/0072884 A1 | 3/2013 | Hamlin et al. |
| 2014/0170208 A1 | 6/2014 | Braun et al. |

FOREIGN PATENT DOCUMENTS

| | | | |
|---|---|---|---|
| CN | EP 2011488 A1 * | 1/2009 | ........... A61K 9/7053 |
| CN | 101032474 B | 2/2011 | |
| CN | 102475692 A | 5/2012 | |
| EP | 593807 A1 | 4/1994 | |
| EP | 0887075 A2 | 12/1998 | |
| EP | 2011488 A1 | 1/2009 | |
| EP | 2172194 A1 | 4/2010 | |
| EP | 2298277 A1 | 3/2011 | |
| JP | H11-60475 A | 3/1999 | |
| JP | 2005023088 A | 1/2005 | |
| JP | 3731016 B2 | 1/2006 | |
| JP | 2009529011 A | 8/2009 | |
| JP | 2011051986 A | 3/2011 | |
| WO | WO0033812 | 6/2000 | |
| WO | WO2004012730 A1 | 2/2004 | |
| WO | WO2005102393 A1 | 11/2005 | |
| WO | WO2006012966 A1 | 2/2006 | |
| WO | WO2008076348 A1 | 6/2008 | |
| WO | WO2009030351 A2 | 3/2009 | |
| WO | WO2009139411 A1 | 11/2009 | |
| WO | WO2009152777 A1 | 12/2009 | |
| WO | WO2011029598 A1 | 3/2011 | |
| WO | WO2011139420 A2 | 11/2011 | |
| WO | WO2012129429 A2 | 9/2012 | |

* cited by examiner

PROPYNYLAMINOINDAN TRANSDERMAL COMPOSITIONS

CROSS-REFERENCE TO RELATED APPLICATIONS

Pursuant to 35 U.S.C. §119 (e), this application is a continuation of U.S. patent application Ser. No. 13/052,955, filed on Mar. 21, 2011, which claims priority to the filing date of: U.S. Provisional Patent Application Ser. No. 61/330,018 filed on Apr. 30, 2010; the disclosure of which application is herein incorporated by reference.

INTRODUCTION

Monoamine oxidases (MAOs) are enzymes that catalyze the oxidation of monoamines, such as monoaminergic neurotransmitters, including dopamine. Because of the role that MAOs play in the inactivation of neurotransmitters, MAO dysfunction (e.g., too much or too little MAO activity) is thought to be responsible for a number of neurological disorders. For example, unusually high or low levels of MAOs in the body have been associated with depression, schizophrenia, substance abuse, attention deficit disorder, migraines, and irregular sexual maturation.

MAOs are found in two main types, MAO type A (MAO-A) and MAO type B (MAO-B). MAO-B is more prevalent in the brain, where it is responsible for the breakdown of dopamine after its release into the synapse. Parkinson's disease is characterized by the death of cells that use dopamine to transmit their signals, which results in a decrease in overall synaptic signal strength and an increase in the symptoms associated with Parkinson's disease.

Rasagiline (i.e., (R)-N-(prop-2-ynyl)-2,3-dihydro-1H-inden-1-amine or R(+)-N-propargyl-1-aminoindan (trade name Azilect®)) is an irreversible inhibitor of monoamine oxidase (MAO) and is selective for MAO type B over MAO type A. By inhibiting the breakdown of dopamine in the synapse, rasagiline permits the signaling neurons to reabsorb more of the released dopamine for reuse later, which may compensate for the diminished quantities of dopamine being produced.

There is a constant need to administer physiologically active agents, such as anti-Parkinson agents (e.g., rasagiline) into human body. Oral administration is the most commonly used method because it is relatively simple to do. However, the oral administration route is often complicated with gastrointestinal irritation and drug metabolism in the liver. Administration through human skin (transdermal drug delivery) is an alternative route to oral administration and can provide some advantages such as the avoidance of first pass metabolism, controlled delivery, more simple dosing regime, and better patient compliance. One major drawback of transdermal route is the limitation of the amount of drug that can be transported across the skin. In order to increase the amount of drug going through skin, drug molecules in free base form are typically used in transdermal route. Drug in free base form is usually not as stable as drug in salt form. Therefore, stability of drug often causes concern. Another approach to increase skin permeation is to use chemical enhancers in the formulation. While delivery through skin can often be increased with the use of enhancers, they often induce more skin irritation.

There are advantages to deliver rasagiline with transdermal route. Rasagiline has relatively high potency and short half life. Oral administration may result in peak-and-valley type plasma profile. Oral administration is often difficult for Parkinsonians. Transdermal rasagiline delivery can provide relatively moderate absorption and can avoid or reduce adverse reaction associated with oral administration, and the dosing frequency can be reduced from daily to every 3 days or even weekly.

SUMMARY

Propynylaminoindan (e.g., Rasagiline) transdermal compositions are provided. Aspects of the transdermal compositions include a matrix of the propynylaminoindan in a pressure sensitive adhesive comprising a carboxylated polymer. In some instances, the matrix further includes a cationic acrylic copolymer. Also provided are methods of using the transdermal compositions and kits containing the transdermal compositions.

Embodiments of the invention provide transdermal rasagiline patches which exhibit desirable active agent delivery properties. As is known in the art, rasagiline has to penetrate across skin in free base form in order to deliver a therapeutic effective dose for sustained period of time, such as up to 7 days. Rasagiline free base is not stable at room temperature and can degrade quickly during room temperature storage. Therefore, the use of rasagiline free base in a transdermal formulation is not a feasible option. To address this degradation issue, rasagiline in salt form, such as rasagiline mesylate, should be used in transdermal formulations since rasagiline salts typically have higher melting points and are more stable. However, a drug is salt form has a very low penetration rate across skin. Embodiments of the invention include transdermal formulations that include a weak base, such as a Eudragit or dimethyl triamine, to facilitate the conversion of rasagiline salt to base. To further balance the conversion from salt to base, e.g., to avoid burst delivery, embodiments of the invention employ pressure sensitive adhesives containing carboxylated functionality. In certain embodiments of the invention, the interaction between the weak base material, drug, and the carboxylated groups in pressure sensitive adhesive provides an optimized delivery of rasagiline across skin, e.g., as described in greater detail below.

DETAILED DESCRIPTION

Figure 1:
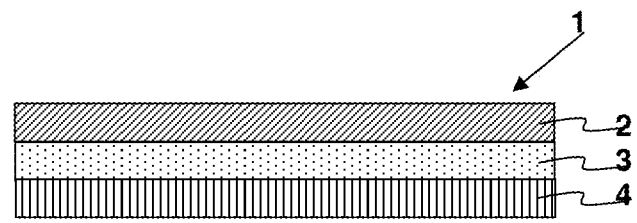
FIG. 1 shows a cross sectional view of an embodiment of the transdermal active agent formulation described herein.

Propynylaminoindan (e.g., Rasagiline) transdermal compositions are provided. Aspects of the transdermal compositions include a matrix of the propynylaminoindan in a pressure sensitive adhesive comprising a carboxylated polymer. In some instances, the matrix further includes a cationic acrylic copolymer. Also provided are methods of using the transdermal compositions and kits containing the transdermal compositions.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various embodiments of the invention, aspects of the transdermal compositions are reviewed first in greater detail, followed by a detailed description of embodiments of using the transdermal delivery systems and a review of kits that include the transdermal delivery systems.

Propynylaminoindan Transdermal Compositions

As summarized above, propynylaminoindan transdermal compositions are provided. Transdermal compositions of the invention are formulations that are configured to transdermally deliver an active agent, specifically a propynylaminoindan, to a subject when topically applied to a skin surface of a subject. The compositions of the invention include a propynylaminoindan active agent layer, wherein the propynylaminoindan active agent layer is formulated to provide for multi-day delivery of a therapeutically effective amount of a propynylaminoindan active agent to a subject when the composition is topically applied to said subject. By multi-day delivery is meant that the layer is formulated to provide a therapeutically effective amount to a subject when the composition is applied to a skin site of a subject for a period of time that is 1 day or longer, such as 2 days or longer, e.g., 3 days or longer, such as 5 days or longer, including 7 days or longer, such as 10 days or longer. By therapeutically effective amount is meant that the compositions, when applied to a skin site of a subject during its intended time of application, e.g., within 7 days of application, provides for a systemic amount of propynylaminoindan that provides a desired therapeutic activity. In some embodiments, the compositions provide delivery of a target dosage of active agent that is 0.5 mg/day or greater over a one week period (i.e., 7 days or 168 hours), including 1.0 mg/day or greater over a one week period, such as 10 mg/day or greater over one week.

Transdermal compositions according to certain embodiments of the invention exhibit a substantially constant flux of the propynylaminoindan active agent over an extended period of time. By substantially constant flux is meant that the magnitude of any variation in flux over the extended period of time is 100% variation in flux or less, such as 80% variation in flux or less and including 50% variation in flux or less, e.g., 40% variation in flux or less, 30% variation in flux or less, such as 25% variation in flux or less, such as 20% variation in flux or less, including 15% variation in flux or less, e.g., 10% variation in flux or less. The extended period of time over which substantially constant flux is observed may vary, and in some instances is 24 hours or longer, such as 48 hours or longer, including 72 hours or longer, e.g., 96 hours or longer. While the actual flux may vary, in some instances (e.g., as determined using the skin permeation assay reported in the Experimental Section, below) skin permeation rates of 0.5 µg/cm²/hr or greater, such as 1 µg/cm²/hr or greater, including 10 µg/cm²/hr or greater are provided by the compositions. In some instances, formulations of the invention exhibit substantially reduced burst delivery of agent immediately following application of the formulation to the skin, e.g., as compared to a control formulation in which the pressure sensitive adhesive does not include carboxylated functionality (such as control pressure sensitive adhesives employed in the Experimental Section, below). By substantially reduced burst deliver is meant a reduction of 10% or more, such as 20% or more, e.g., 25% or more, 33% or more, 40% or more, 50% or more, including 66% or more, 75% or more, including 90% or more. In some instances, the formulations are configured to provide substantially zero-order delivery of the active agent.

The size (i.e., area) of the transdermal compositions may vary. In certain embodiments, the size of the composition is chosen in view of the desired transdermal flux rate of the active agent and the target dosage. For example, if the transdermal flux is 3.4 μg/cm²/hr and the target dosage is 5 mg/day, then the transdermal composition is chosen to have an area of about 43 cm². Or for example, if the transdermal flux is 3.4 μg/cm²/hr and the target dosage is 10 mg/day, then the transdermal patch is chosen have an area of about 87 cm². In certain embodiments, the compositions have dimensions chosen to cover an area of skin when applied to a skin site that ranges from 10 to 200, such as 20 to 150, including 40 to 140 cm².

The propynylaminoindan active agent layer of the compositions may vary in thickness. In some instances, the thickness of the active agent layer (i.e., matrix) ranges from 25 to 250, such as 50 to 200, including 100 to 150 micrometers in thickness.

In some embodiments, the compositions of the invention include a propynylaminoindan active agent layer, a backing layer and release liner. For example, FIG. 1 a composition 1 according to an embodiment of the invention, where the composition 1 includes a backing layer 2, a propynylaminoindan active agent layer 3 (i.e., matrix), and a release liner 4. Each of these layers is now described in greater detail.

Matrix

As reviewed above, transdermal compositions of invention include an active agent containing matrix present on a surface of a backing. Matrix layers of interest include an amount of propynylaminoindan active agent present in a pressure sensitive adhesive. Propynylaminoindans of interest include compounds that are described above the formula:

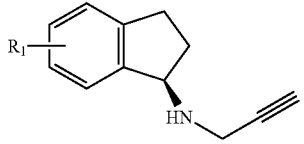

wherein $R_1$ is H, —$OR_2$, or

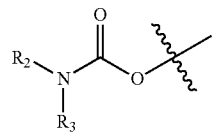

wherein $R_2$ is $C_1$-$C_4$ alkyl, and $R_3$ is H or $C_1$-$C_4$ alkyl. In some instances, the propynylaminoindan is N-propargyl-1-aminoindan (i.e., Rasagiline).

The propynylaminoindan active agent may be present in the matrix as a free base or salt. Pharmaceutically acceptable salts include, but are not limited to, the mesylate, maleate, fumarate, tartrate, hydrochloride, hydrobromide, esylate, p-toluenesulfonate, benzoate, acetate, phosphate and sulfate salts. In addition, the propynylaminoindan may be present as a racemic mixture or as a pure enantiomer, such as the R or L enantiomer of the active agent.

In some instances, the propynylaminoindan in the matrix is solely R(+)-N-propargyl-1-aminoindan free base. In some instances, the propylnylaminoindan is solely R(+)-N-propargyl-1-aminoindan mesylate.

The amount of propynylaminoindan present in the matrix may vary. In some instances, the amount of propynylaminoindan may range from 5 mg to 50 mg, such as 10 mg to 40 mg and including 15 mg to 30 mg.

As reviewed above, the matrix includes a pressure sensitive adhesive. The terms "pressure sensitive adhesive", "self adhesive", and "self stick adhesive" mean an adhesive that forms a bond when pressure is applied to adhere the adhesive with a surface. In some instances, the adhesive is one in which no solvent, water, or heat is needed to activate the adhesive. For pressure sensitive adhesives, the degree of bond strength is proportional to the amount of pressure that is used to apply the adhesive to the surface.

Pressure sensitive adhesives of interest include, but are not limited to carboxylated polymer, such as carboxylated acrylate copolymers. Acrylate copolymers of interest include copolymers of various monomers which may be "soft" monomers, "hard" monomers, and optionally "functional" monomers. Also of interest are blends including such copolymers. The acrylate copolymers can be composed of a copolymer including bipolymer (i.e., made with two monomers), a terpolymer (i.e., made with three monomers), or a tetrapolymer (i.e., made with four monomers), or copolymers made from even greater numbers of monomers. The acrylate copolymers can include cross-linked and non-cross-linked polymers. The polymers can be cross-linked by known methods to provide the desired polymers.

Monomers from which the acrylate copolymers are produced include at least two or more exemplary components selected from the group including acrylic acids, alkyl acrylates, methacrylates, copolymerizable secondary monomers or monomers with functional groups. Monomers ("soft" and "hard" monomers) of interest include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989).

Of interest are acrylate copolymers that include polar functional monomeric residues. Of specific interest are monomeric residues that provide for —COOH functional groups. Useful carboxylic acid monomers to provide the —COOH functional group may contain from about 3 to about 6 carbon atoms and include, among others, acrylic acid, methacrylic acid, itaconic acid, and the like. Acrylic acid, methacrylic acid and mixtures thereof are employed in certain embodiments acids. The functional monomer(s) are present in certain embodiments of the copolymers in an amount of 2 wt % or more, such as between 3-10 wt %.

In some embodiments, the adhesive may have a composition that is, or is substantially the same as, the composition of DuroTak® 87-2852 (Henkel, Bridgewater, N.J.). The term "substantially the same" as used herein refers to a composition that is an acrylate-vinyl acetate copolymer in an organic solvent solution and provides for the functionality as described herein. In some embodiments, the acrylic pressure-sensitive adhesive is DuroTak® 87-2852.

In some instances, the pressure sensitive adhesive may make up from 50 to 95, such as 60 to 90 and including 65 to 85% by weight of the matrix.

When the propynylaminoindan is present as a free base, the matrix may consist of the active agent and pressure sensitive adhesive, such as DuroTak® 87-2852 pressure sensitive adhesive.

In some instances, e.g., where the propynylaminoindan is present as a salt, the matrix may further include a weak base, such as a cationic acrylic copolymer. Cationic acrylic copolymers of interest are polymers of two or more different monomeric residues, where at least one of the residues is an acrylic residue, e.g., an acrylate or a methacrylate, and at least one of the residues includes a cationic pendant group, e.g., an amino pendant group, where these features may be includes in the same or different monomeric residues making up the copolymer. Where desired, the cationic acrylic copolymer may be aminated methacrylate copolymer. The aminated methacrylate copolymer may be a copolymer of diethylaminoethyl methacrylate, butyl methacrylate and methyl methacrylate. Of interest are aminated methacrylate copolymers that are substantially the same as Eudragit® E100 aminated methacrylate copolymer. As used herein, the term substantially the same is meant that the aminated methacrylate copolymer has the same functional impact on the composition as Eudragit® E100 aminated methacrylate copolymer. In some instances, the aminated methacrylate copolymer is Eudragit® E100 aminated methacrylate copolymer. If present, the amount of cationic acrylic copolymer may be present in an amount ranging from 1 to 15, such as 2 to 10 and including 4 to 8% by weight of the matrix. Also of interest as weak bases are agents such as triethanolamine. If present, the amount of triethanolamine may be present in an amount ranging from 1 to 15, such as 2 to 10 and including 4 to 8% by weight of the matrix.

The matrix as described herein may contain a percutaneous absorption enhancer. The percutaneous absorption enhancer may facilitate the absorption of the active agent by the skin of the subject. The percutaneous absorption enhancer may also be referred to as a percutaneous permeation enhancer because it may facilitate not only the percutaneous absorption of the active agent, but also the percutaneous permeation of the active agent through the skin of the subject.

The percutaneous absorption enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —O—CH$_2$CH$_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives; and combinations thereof.

Additional types of percutaneous absorption enhancers include, but are not limited to lactic acid, tartaric acid, 1,2,6-hexanetriol, benzyl alcohol, lanoline, potassium hydroxide (KOH), and tris(hydroxymethyl)aminomethane.

Specific examples of percutaneous absorption enhancers include, but are not limited to glycerol monooleate (GMO), sorbitan monolaurate (SML), sorbitan monooleate (SMO), laureth-4 (LTH), and combinations thereof.

In some cases, the matrix contains the percutaneous absorption enhancer in an amount ranging from 2% to 25% (w/w), such as from 5% to 20% (w/w), and including from 5% to 15% (w/w). In certain cases, the matrix contains the percutaneous absorption enhancer in an amount of about 5% (w/w), about 10% (w/w), about 15% (w/w), or about 20% (w/w).

In some embodiments, the matrix layer is insoluble in water. By insoluble in water is meant that that the matrix layer may be immersed in water for a period of 1 day or longer, such as 1 week or longer, including 1 month or longer, and exhibit little if any dissolution, e.g., no observable dissolution.

Backing

As summarized above, transdermal compositions of interest may include a backing (i.e., support layer). The backing may be flexible to an extent that it can be brought into close contact with a desired topical location of a subject. The backing may be fabricated from a material that it does not absorb the active agent, and does not allow the active agent to be released from the side of the support. The backing may include, but is not limited to, non-woven fabrics, woven fabrics, films (including sheets), porous bodies, foamed bodies, paper, composite materials obtained by laminating a film on a non-woven fabric or fabric, and combinations thereof.

Non-woven fabric may include, but is not limited to, the following: polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include, but are not limited to: cotton, rayon, polyacrylic resins, polyester resins, polyvinyl alcohol, and combinations thereof. Films may include, but are not limited to the following: polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof.

Papers may include, but are not limited to, impregnated paper, coated paper, wood free paper, Kraft paper, Japanese paper, glassine paper, synthetic paper, and combinations thereof. Composite materials may include, but are not limited to, composite materials obtained by laminating the above-described film on the above-described non-woven fabric or fabric.

The size of the backing may vary, and in some instances the backing is sized to cover the desired topical target site. In some embodiments, the backing has a length ranging from 2 to 100 cm, such as 4 to 60 cm and a width ranging from 2 to 100 cm, such as 4 to 60 cm.

In some embodiments, the backing layer is insoluble in water. By insoluble in water is meant that that the backing layer may be immersed in water for a period of 1 day or longer, such as 1 week or longer, including 1 month or longer, and exhibit little if any dissolution, e.g., no observable dissolution.

Release Liner

In some embodiments, a release liner is provided on the active agent layer (i.e., matrix), and specifically on a surface of the active agent layer that is distal (i.e. opposite) from the backing layer, if present. The release liner facilitates the protection of the active agent layer. The release liner may be prepared by treating one side of polyethylene-coated wood free paper, polyolefin-coated glassine paper, a polyethylene terephthalate (polyester) film, a polypropylene film, or the like with a silicone treatment.

Adhesive Overlay

Optionally, one or more adhesive overlays can be used to increase the adhesion of the composition when applied to the skin. Adhesive overlays can include a layer of adhesive present on a backing material, such as a porous, non-porous, occlusive, or breathable backing material. The dimensions of the adhesive overlay are chosen to provide the desired functionality, where in some instances the dimensions are chose such that the adhesive overlay, when applied over the active agent formulation, extends some distance beyond one or more of the sides of the active agent formulation. In some instances, the area of the adhesive overlay exceeds the area of the active agent formulation by 5% or more, such as by 10% or more, including by 20% or more. During use, the adhesive overlay can be applied by the patients, by the care givers, or can be integrated in the kits.

Methods of Use

Methods of using the product transdermal compositions include administering an effective amount of the propynylaminoindan composition to a subject in order to treat the subject for a target condition of interest, e.g., as described in the Utility section below. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the transdermal compositions disclosed herein can be topically administered to a subject, i.e., the transdermal compositions may be administered to any convenient topical site (e.g., skin site). Topical sites of interest include both mucosal sites and keratinized skin sites, and therefore include, but are not limited to: mouth, nose, eyes, rectum, vagina, arms, leg, torso, head, etc. The surface area that is covered by the topical composition following application is sufficient to provide for the desired amount of agent administration, and in some embodiments ranges from 1 to 200 cm$^2$, such as from 10 to 180 cm$^2$, and including from 100 to 150 cm$^2$, e.g., 140 cm$^2$.

The transdermal composition may be maintained at the topical site to which it has been applied for a desired amount of time, e.g., to deliver a desired amount of active agent delivery. In some instances, the period of time that the composition is maintained at the site of application is 24 hours or longer, such as 48 hours or longer, e.g., 72 hours or longer, such as 96 hours or longer.

In practicing the subject methods, a given dosage of the transdermal composition may be applied a single time or a plurality of times over a given time period, e.g., the course of the disease condition being treated, where the dosing schedule when a plurality of compositions are administered over a given time period may be daily, weekly, biweekly, monthly, etc.

The area of skin covered by the topical composition when applied may vary. In some instances, the area of skin covered by the topical composition upon application ranges from 1 to 200 cm$^2$, such as 10 to 180 cm$^2$ and including 100 to 150 cm$^2$.

After the transdermal active agent composition has been applied to the skin site for the desired amount of time (i.e., an amount of time sufficient to deliver a target dose of the active agent to the subject over a period of time), the composition may be removed from the skin site. A new transdermal composition may be applied at the same or at a different skin site. The new transdermal composition may be applied to a different skin site to reduce the possible occurrence of skin irritation and/or skin sensitization at the prior site of application.

In certain embodiments, the subject methods include a diagnostic step. Individuals may be diagnosed as being in need of the subject methods using any convenient protocol. In addition, individuals may be known to be in need of the subject methods, e.g., they are suffering from Parkinson's disease. Diagnosis or assessment of target condition can be performed using any convenient diagnostic protocol.

Methods of the invention may further include assessing the efficacy of the treatment protocol that includes administration of the local anesthetic emulsion composition. Assessing the efficacy of treatment may be performed using any convenient protocol.

In some instances, transdermal compositions may be administered in conjunction with one or more additional therapies specific for the target condition of interest. As such, the transdermal compositions may be used alone to treat the target disorder, or alternatively, as in the case of Parkinson's disease, for example, they may be used as an adjunct to the conventional L-DOPA treatments.

Transdermal compositions of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

Utility

The transdermal compositions of the invention find use in any application where a subject would benefit from being transdermally administered a propynylaminoindan, such as rasagiline. Rasagiline and/or its salts find use in the treatment of a variety of different disease conditions, such as but not limited to: Parkinson's disease, Alzheimer's Disease, memory disorders, stroke and other disorders, e.g., as described in U.S. Pat. Nos. 5,387,612; 5,453,446; 5,457, 133; 5,668,181; 5,576,353; 5,532,415; 5,599,991; 5,786, 390; 5,519,061; 5,891,923; 5,744,500 and 6,316,504, the contents of which are hereby incorporated by reference. By treatment is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition.

Kits

Kits for use in practicing certain methods described herein are also provided. In certain embodiments, the kits include one or more transdermal compositions as described above. In certain embodiments, the kits include an adhesive overlay as described above. In some embodiments, the kits include multilayers such as a layer containing drug and a layer that may or may not contain any drug and other excipients. In a given kit that includes two or more compositions, the compositions may be individually packaged or present within a common container.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples are offered by way of illustration and not by way of limitation. Specifically, the following examples are of specific embodiments for carrying out the present invention. The examples are for illustrative purposes only, and are not intended to limit the scope of the present invention in any way.

Examples

I. Materials and Methods

A. Preparation of Active Agent Reservoir Layer

Formulations were prepared by mixing stock solutions of each of the mixture components in organic solvents (typically 30-60 wt % solid content in ethyl acetate, methanol and/or ethanol), followed by a mixing process. Once a homogeneous mixture was formed, the solution was cast on a release liner (siliconized polyester sheet of 2-3 mils) and dried at 65°-80° C. for 10-90 minutes. The adhesive films were laminated to a PET backing.

B. Transdermal Flux Tests

Human cadaver skin was used and epidermal layers (stratum corneum and epidermis) were separated from the full-thickness skin as skin membrane. Samples were die-cut with an arch punch to a final diameter of about 2.0 cm$^2$. The release liner was removed and the system was placed on top of the epidermis/stratum corneum with the drug adhesive layer facing the stratum corneum. Gentle pressure was applied to effect good contact between the adhesive layer and stratum corneum. The donor and receptor sides of the Franz cell were clamped together and the receptor solution containing a phosphate buffer at pH 6.5 was added to the Franz cell. The cells were kept at 33° C. for the duration of the experiment. Samples of the receptor solution were taken at regular intervals and the active agent concentration was measured by HPLC. The removed receptor solution was replaced with fresh solution to maintain the sink conditions. The flux was calculated from the slope of cumulative amounts of the drug in the receiver compartment versus time plot.

C. Specific Examples

C.1 Flux of Rasagiline Base in Acrylate Adhesive

Loading Effect

Figure 2:
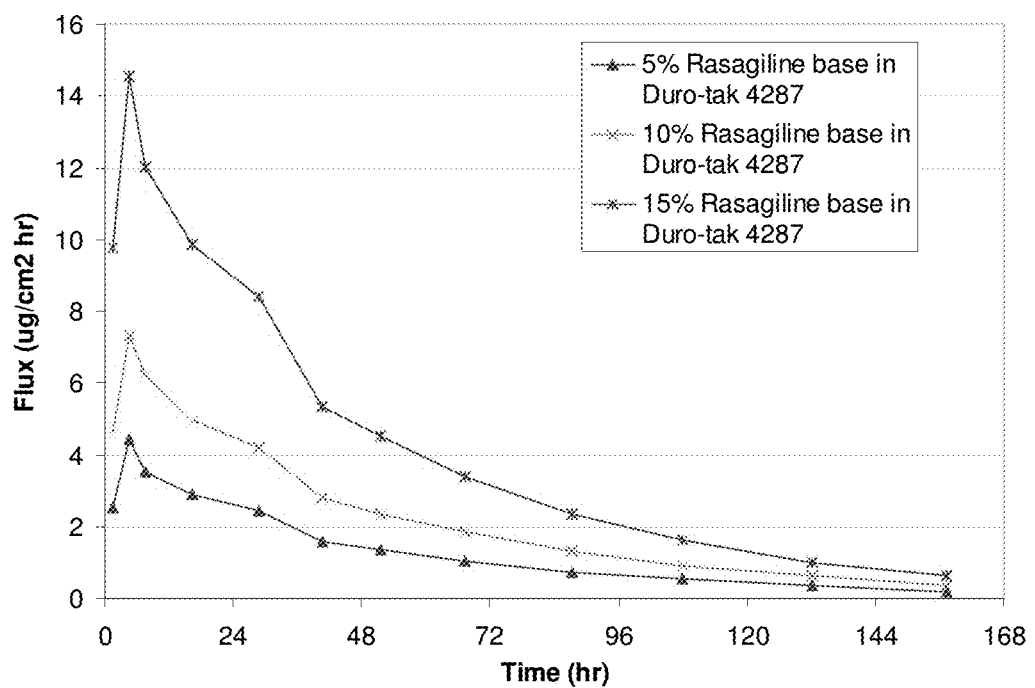
FIGS. 2 to 8 show graphs of flux as a function of time (middle point between the two sampling time points) for various formulations.

Using the general method described previously, a series of transdermal systems containing different rasagiline base loadings in Duro-Tak® 87-4287 were prepared with details shown in following table. The flux through human cadaver skin was measured and the results are graphically presented in FIG. 2. Significant rasagiline base loading effect was observed. There is also a burst flux at the beginning followed by significant decrease in flux. Since rasagiline is a potent drug with 1 mg daily dosage, burst flux with high flux rate is not desirable.

TABLE 1

| Sample | Adhesive | Drug loading |
|---|---|---|
| 1 | Duro-tak ® 87-4287 | 5% |
| 2 | Duro-tak ® 87-4287 | 10% |
| 3 | Duro-tak ® 87-4287 | 15% |

C.2 Flux of Rasagiline Base in PIB Adhesive

Loading Effect

Figure 3:
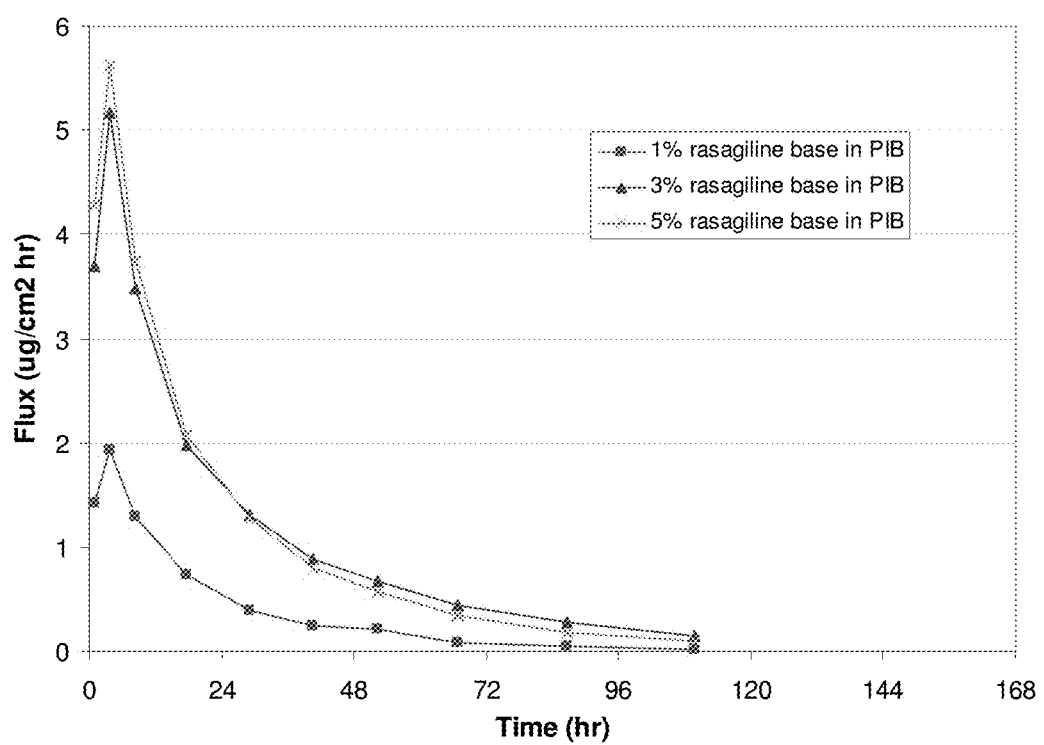

Using the general method described previously, a series of transdermal systems containing different rasagiline base loadings in a PIB adhesive were prepared with details shown in following table. The flux through human cadaver skin was measured and the results are graphically presented in FIG. 3. The PIB adhesive is formulated with PIB Oppanol B10, Oppanol B30, and polybutylene H1900 with ratio of 6:6:1.

TABLE 2

| Sample | Adhesive | Drug loading |
|---|---|---|
| 1 | PIB | 1% |
| 2 | PIB | 3% |
| 3 | PIB | 5% |

C.3 Flux of Rasagiline Base in Silicone

Using the general method described previously, transdermal systems containing rasagiline base in a silicone adhesive (Bio-PSA 7-4101) were prepared with details shown in following table. The flux through human cadaver skin was measured. The steady state flux was found to be around 0.1 µg/hr·cm². Bio-PSA 7-4101 is supplied by Dow Corning. It is amine-compatible pressure sensitive adhesive with 65/35 resin to polymer ratio. It is supplied as a 60% solid content solution in heptane.

TABLE 3

| Sample | Adhesive | excipient | Drug loading | Steady state flux (µg/hr · cm²) |
|---|---|---|---|---|
| 1 | 95% Bio-PSA 7-4101 | none | 5% rasagiline base | 0.1 |
| 2 | 80% Bio-PSA 7-4101 | 15% silicone oil | 5% rasagiline base | 0.1 |

C.4 Flux of Rasagiline Mesylate in Acrylate Adhesive

Eudragit E100 Loading Effect

Figure 4:
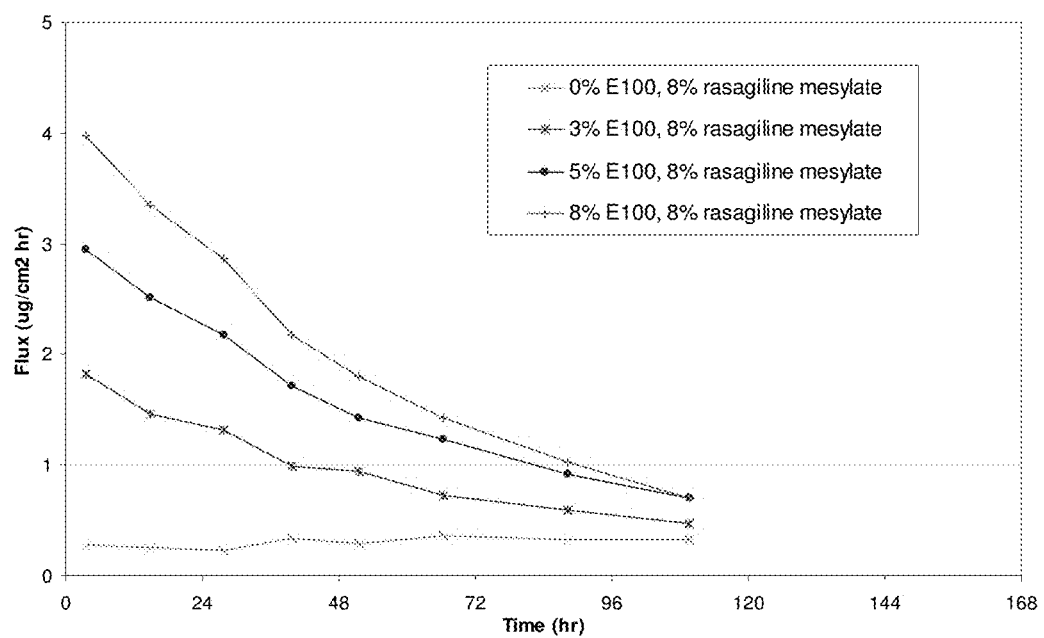

Using the general method described previously, a series of transdermal systems containing different Eudragit E100 loadings in acrylate adhesive were prepared with details shown in the following table. The flux through human cadaver skin was measured and the results are graphically presented in FIG. 4. The data here illustrated the interaction between rasagiline mesylate and weak base Eudragit. The use of Eudragit E100 plays significant role to increase flux across skin when rasagiline mesylate is used in the patch system.

TABLE 4

| Sample | Adhesive | Excipient | Rasagiline mesylate loading |
|---|---|---|---|
| 1 | Duro-tak ® 87-4287 | 0% E100 | 8% |
| 2 | Duro-tak ® 87-4287 | 3% E100 | 8% |
| 3 | Duro-tak ® 87-4287 | 5% E100 | 8% |
| 4 | Duro-tak ® 87-4287 | 8% E100 | 8% |

C.5 Flux of Rasagiline Mesylate in Acrylate Adhesive

Adhesive Effect

Figure 5:
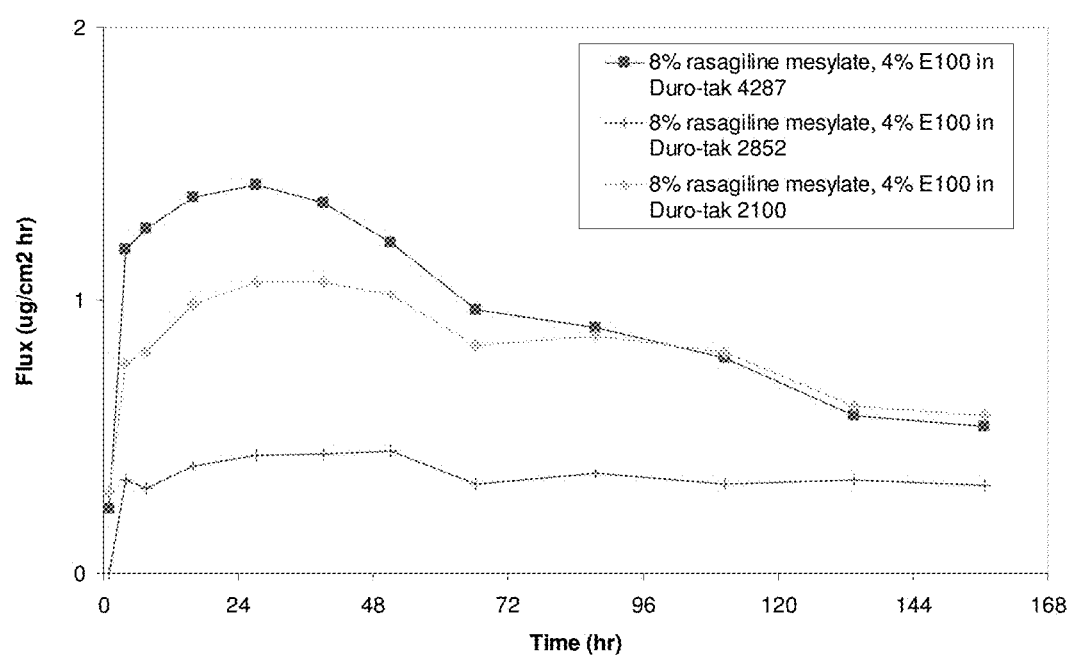

Using the general method described previously, a series of transdermal systems containing different acrylate adhesive was prepared with details shown in the following table. The flux through human cadaver skin was measured and the results are graphically presented in FIG. 5. One major difference between these 3 acrylate adhesives is the content of COOH functionality. Duro-Tak® 87-4287 contains no COOH groups while Duro-Tak® 87-2100 and Duro-Tak® 87-2852 contain different amounts of COOH groups. The data here illustrated the interaction between rasagiline mesylate, Eudragit E100, and COOH groups in adhesive. For the system with adhesive without COOH group, there is also a burst delivery at the beginning although it is not as significant as the system containing rasagiline base. This burst delivery can be significantly reduced with using adhesive containing COOH groups. Sample #3 has the highest COOH concentration and presents the flattest delivery. A close to zero order delivery profile is often desirable in controlled delivery.

TABLE 5

(#12)

| Sample | Adhesive | Excipient | Rasagiline mesylate loading |
|---|---|---|---|
| 1 | Duro-tak ® 87-4287 | 4% E100 | 8% |
| 2 | Duro-tak ® 87-2100 | 4% E100 | 8% |
| 3 | Duro-tak ® 87-2852 | 4% E100 | 8% |

C.6 Flux in Acrylate Adhesive

Adhesive Effect

Figure 6:
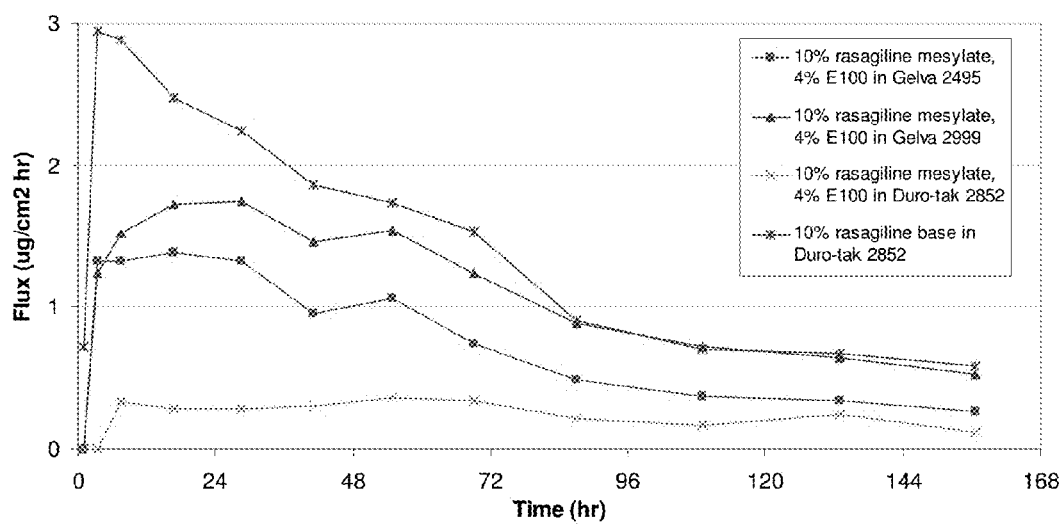

Using the general method described previously, a series of transdermal systems containing different acrylate adhesive was prepared with details shown in the following table. The flux through human cadaver skin was measured and the results are graphically presented in FIG. 6. The data here illustrated the interaction between rasagiline mesylate, Eudragit E100, and COOH groups in adhesive.

TABLE 6

| Sample | Adhesive | Excipient | Drug loading |
|---|---|---|---|
| 1 | Gelva 2495 | 4% E100 | 10% rasagiline mesylate |
| 2 | Gelva 2999 | 4% E100 | 10% rasagiline mesylate |
| 3 | Duro-tak ® 87-2852 | 4% E100 | 10% rasagiline mesylate |
| 4 | Duro-tak ® 87-2852 | none | 10% rasagiline base |

C.7 Flux in Acrylate Adhesive

Multi-Layer Design

Figure 7:
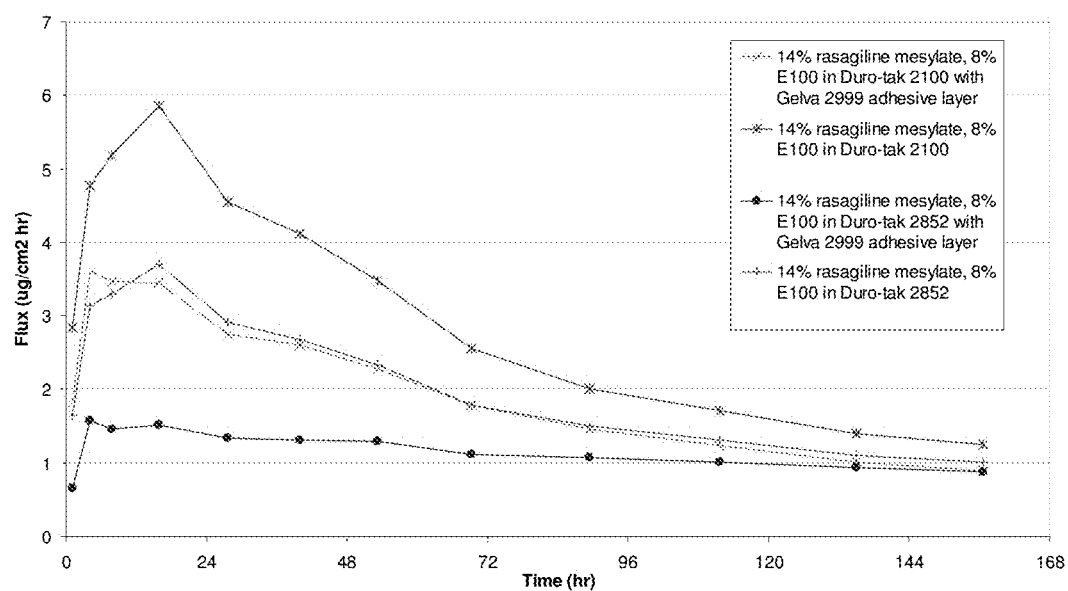

Using the general method described previously, a series of transdermal systems containing different acrylate adhesives and different design was prepared with details shown in the following table. The flux through human cadaver skin was measured and the results are graphically presented in FIG. 7. Both rasagiline mesylate and E100 were loaded in drug layer. The use of adhesive layer can serve the purpose to control skin adhesion.

TABLE 7

| | Formulation | | | Rasagiline mesylate loading |
|---|---|---|---|---|
| Sample | Drug layer | Adhesive layer | Excipient | |
| 1 | Duro-tak ® 87-2100 | none | 8% E100 | 14% |
| 2 | Duro-tak ® 87-2100 | Gelva 2999 | 8% E100 | 14% |
| 3 | Duro-tak ® 87-2852 | Gelva 2999 | 8% E100 | 14% |
| 4 | Duro-tak ® 87-2852 (50%) Gelva 2999 (50%) | none | 6% E100 | 10% |

C.8 Flux in Acrylate Adhesive

Adhesive and Excipient Effect

Figure 8:
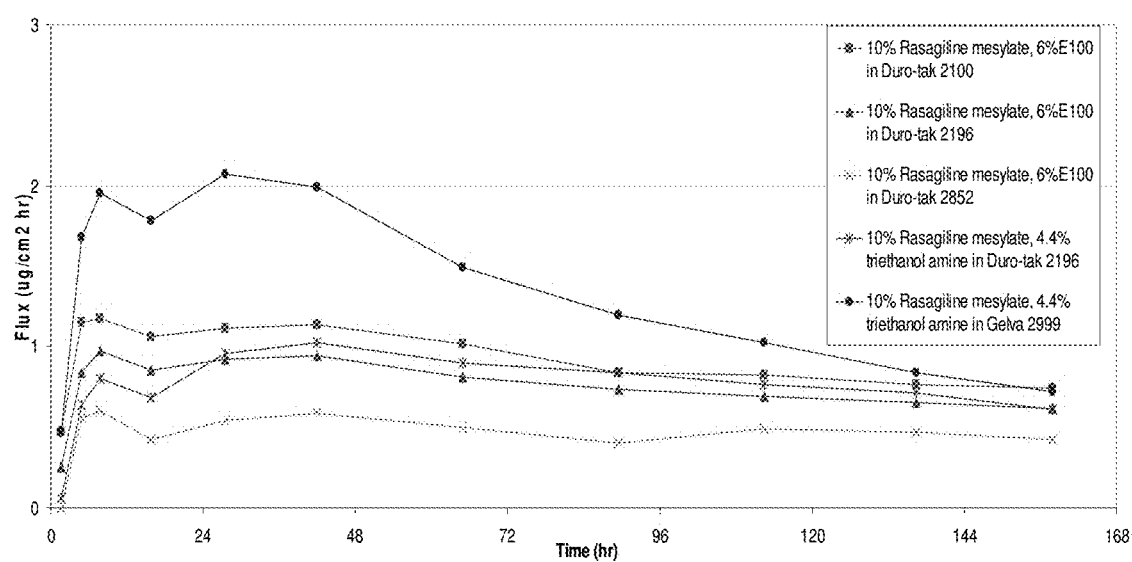

Using the general method described previously, a series of transdermal systems containing different acrylate adhesive and different basic excipients was prepared with details shown in the following table. The flux through human cadaver skin was measured and the results are graphically presented in FIG. 8. The data here showed that Eudragit E100 can be replaced with other weak bases with similar properties.

TABLE 8

| Sample | Adhesive | Excipient | Drug loading |
|---|---|---|---|
| 1 | Duro-tak ® 87-2100 | 6% E100 | 10% rasagiline mesylate |
| 2 | Duro-tak ® 87-2196 | 6% E100 | 10% rasagiline mesylate |
| 3 | Duro-tak ® 87-2852 | 6% E100 | 10% rasagiline mesylate |
| 4 | Duro-tak ® 87-2196 | 4.4% triethanol amine | 10% rasagiline mesylate |
| 5 | Gelva 2999 | 4.4% triethanol amine | 10% rasagiline mesylate |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   applying to a skin surface of a subject a transdermal composition comprising:
   a matrix comprising:
   an N-propargyl-1-aminoindan in an amount of 5% to 15% by weight of the matrix;
   a pressure sensitive adhesive comprising an acrylate-vinyl acetate copolymer comprising —COOH functional groups and a crosslinker; and
   an aminated methacrylate copolymer comprising diethylaminoethyl methacrylate, butyl methacrylate and methyl methacrylate in an amount of 2% to 10% by weight of the matrix; and
   a backing;
   in a manner sufficient to achieve a constant flux of the N-propargyl-1-aminoindan that varies by 30% or less over an extended period of time of 72 hours or longer.

2. The method according to claim 1, wherein the N-propargyl-1-aminoindan is present as a salt.

3. The method according to claim 1, wherein the matrix further comprises an enhancer.

4. The method according to claim 1, wherein the matrix consists of R(+)-N-propargyl-1-aminoindan mesylate, the aminated methacrylate copolymer comprising diethylaminoethyl methacrylate, butyl methacrylate and methyl methacrylate, and the pressure sensitive adhesive comprising an acrylate-vinyl acetate copolymer comprising —COOH functional groups and a crosslinker.

5. The method according to claim 1, wherein the N-propargyl-1-aminoindan is R(+)-N-propargyl-1-aminoindan.

6. The method according to claim 5, wherein the N-propargyl-1-aminoindan is R(+)-N-propargyl-1-aminoindan mesylate.

7. The method according to claim 1, wherein the flux of the N-propargyl-1-aminoindan varies by 25% or less.

* * * * *